US008882670B2

(12) United States Patent
Hancock

(10) Patent No.: US 8,882,670 B2
(45) Date of Patent: Nov. 11, 2014

(54) APPARATUS AND METHOD FOR MEASURING CONSTITUENT CONCENTRATIONS WITHIN A BIOLOGICAL TISSUE STRUCTURE

(75) Inventor: Christopher Paul Hancock, Bath & North East Somerset (GB)

(73) Assignee: Credent Medical Limited, Liverpool (GB)

( * ) Notice: Subject to any disclaimer, the term of this patent is extended or adjusted under 35 U.S.C. 154(b) by 1612 days.

(21) Appl. No.: 11/994,818

(22) PCT Filed: Jul. 6, 2006

(86) PCT No.: PCT/GB2006/002514
§ 371 (c)(1),
(2), (4) Date: Jul. 9, 2008

(87) PCT Pub. No.: WO2007/003955
PCT Pub. Date: Jan. 11, 2007

(65) Prior Publication Data
US 2008/0319285 A1    Dec. 25, 2008

(30) Foreign Application Priority Data

Jul. 6, 2005  (GB) .................................. 0513810.2
Jul. 26, 2005 (GB) .................................. 0515277.2

(51) Int. Cl.
*A61B 5/00* (2006.01)
*A61B 5/05* (2006.01)
*A61B 5/145* (2006.01)

(52) U.S. Cl.
CPC .......... *A61B 5/14546* (2013.01); *A61B 5/0507* (2013.01); *A61B 5/14532* (2013.01); *A61B 5/05* (2013.01)
USPC ........................... 600/309; 600/430; 600/316

(58) Field of Classification Search
USPC ......................................... 600/309, 430, 316
See application file for complete search history.

(56) References Cited

U.S. PATENT DOCUMENTS

| 2003/0036713 | A1* | 2/2003 | Bouton et al. ................. 600/587 |
| 2004/0065158 | A1* | 4/2004 | Schrepfer et al. .......... 73/864.81 |
| 2004/0127777 | A1* | 7/2004 | Ruchti et al. .................. 600/316 |
| 2004/0133086 | A1* | 7/2004 | Ciurczak et al. .............. 600/322 |

FOREIGN PATENT DOCUMENTS

WO    WO 02/069791 A    9/2002

OTHER PUBLICATIONS

Kim "On Measuring Glucose Concentration in Solutions Using Radio Frequency Microwave" 2004, as submitted by applicant.*
International Search Report for International Application No. PCT/GB2006/002514 dated Nov. 27, 2006.

(Continued)

*Primary Examiner* — Max Hindenburg
*Assistant Examiner* — Renee Danega
(74) *Attorney, Agent, or Firm* — Marshall, Gerstein & Borun LLP

(57) ABSTRACT

Apparatus for minimally invasively measuring concentrations of constituents contained within a biological tissue structure includes a microwave energy source arranged generate a range of microwave frequencies, a first antenna coupled to the microwave energy source and arranged to transmit at least a portion of the microwave energy into the tissue structure, a second antenna arranged to receive at least a portion of the microwave energy transmitted through the tissue structure, a signal processor arranged to determine the resonant frequency of the received microwave energy, and a data processor arranged to provide an output of the concentration of constituents within the biological tissue structure according to the determined resonant frequency.

45 Claims, 12 Drawing Sheets

(56) References Cited

OTHER PUBLICATIONS

Kim, T.W., et al. "On Measuring Glucose Concentration in Solutions Using Radio Frequency Microwave," IEICE Transactions on Information and Systems, Information & Systems Society, Tokyo, JP, vol. E87-D, No. 12, Dec. 2004, pp. 2905-2908, XP008071727, ISSN: 0916-8532.

Yansheng Xu et, al. "On the Measurement of Microwave Permittivity of Biological Samples Using Needle-Type Coaxial Probes," IEEE Transactions on Instrumentation and Measurement, IEEE Service Center, Piscataway, NJ, US, vol. 42, No. 4, Aug. 1, 1993, pp. 822-827, XP000399898, ISSN: 0018-9456.

Nikawa Y., et al. "Application of millimeter waves to measure blood sugar level," Microwave Conference, 2001. APMC 2001. 2001 Asia-Pacific, Dec. 3-6, 2001, Piscataway, NJ USA, IEEE, vol. 3, Dec. 3, 2001, pp. 1303-1306, XP010578857 ISBN: 0-7803-7138-0.

Land D.V., et al. "A quick accurate method for measuring the microwave dielectric properties of small tissue samples," Physics in Medicine and Biology, Taylor and Francis Ltd., London, GB, vol. 37, No. 1, Jan. 1, 1992, pp. 183-192, XP020021930, ISSN: 0031-9155.

\* cited by examiner

APPARATUS AND METHOD FOR MEASURING CONSTITUENT CONCENTRATIONS WITHIN A BIOLOGICAL TISSUE STRUCTURE

BACKGROUND

Diabetes mellitus (diabetes) is a disease in which the body does not produce or properly use insulin. In simplest terms, insulin is a hormone needed to convert sugar and starches into energy. In effect, insulin is the hormone that unblocks cells of the body, allowing glucose to enter these cells to provide food to keep them alive. If glucose cannot enter the cells, the glucose concentration in the body builds up and, without treatment, the cells within the body end up starving to death. The measurement of blood-glucose is thus perhaps the most important measurement in medicine, as diabetes has immense public health implications. Diabetes is currently a leading cause of disability and death throughout the world.

Diabetes sufferers cannot moderate the amount of glucose in their bloodstream automatically in the manner non-sufferers can. Therefore to prevent the onset and the progression of complications associated with diabetes, sufferers of both Type I (where the body fails to produce sufficient insulin) and Type II diabetes (where the body develops a resistance to the action of its own insulin) are advised to closely monitor the concentration of glucose in their bloodstream. If the concentration is outside the normal healthy range, the patient needs to adjust his or her insulin dosage or sugar intake to counter the risk of diabetic complications.

The most common method of measuring blood-glucose level requires blood to be withdrawn from the patient. The conventional procedure involves pricking the finger, or other body part, to withdraw blood, and then to test the blood for glucose levels, either by depositing one or more drops onto a reagent carrier strip having a glucose testing substance thereon that changes colour or shading in correspondence with the detected amount of blood-glucose, or by the use of a portable, often hand held, electronic testing device. However, many people find this method either inconvenient, painful, difficult to perform or simply unpleasant.

A further common glucose monitoring method involves urine analysis. This method tends to be most inconvenient and may not reflect the current status of the blood-glucose level due to the fact that glucose appears in the urine only after a significant period of elevated levels of blood-glucose.

Another technique involves using implantable medical devices to measure cardiac signals. In one such invention, the blood-glucose levels are determined based on T-wave amplitude and the QT-interval. The disadvantage of this method is that the instrument has to be inserted inside the human body and so a complex medical procedure may need to be performed. Also, the patient would need to be admitted to hospital and may need to stay for a few days. Additionally, this device would be classified as a class III medical device because it is inserted inside the body. A class III medical device is categorised as a high-risk device and would need to go through stringent testing and validation procedures before being granted approval by the medical devices regulatory bodies to enable it to be put into regular use.

A further measurement technique involves the sampling of interstitial fluid from the skin. A system developed by Cygnus Inc., known as the GlucoWatch G2 Biographer, uses low levels of electrical current to extract glucose molecules through the skin. The glucose is extracted from interstitial fluid that surrounds skin cells, rather than from blood. The system gathers and analyses current-time and charge time data to calculate blood-glucose level information. The drawbacks of this system are; it is still necessary to perform the finger prick test in order to calibrate the system and it is still necessary to withdraw a small amount of biological fluid (interstitial fluid) from the body during normal operation.

Many attempts have also been made to develop a painless, patient friendly, cost effective, non-invasive instrument to monitor blood-glucose levels. The non-invasive approaches considered include: electrochemical, spectroscopic technologies, such as near infrared spectroscopy, Ramen Spectroscopy and small scale NMR, measurements on lacrimal fluid (self-sampled tears), and acoustic velocity measurement techniques. However, none of these methods appear to have produced a marketable device or method for in-vivo measurement of blood-glucose level that is sufficiently accurate, reliable, patient friendly, convenient and cost-effective enough to be used in routine use.

SUMMARY OF THE INVENTION

According to a first aspect of the present invention there is provided apparatus for minimally invasively or non-invasively measuring concentrations of constituents contained within a biological tissue structure, the apparatus comprising a microwave energy source arranged to generate a range of microwave frequencies, a first antenna coupled to the microwave energy source and arranged to transmit at least a portion of the microwave energy into the tissue structure, a second antenna arranged to receive at least a portion of the microwave energy transmitted through the tissue structure, a signal processor arranged to determine the resonant frequency of the received microwave energy and a data processor arranged to provide an output of the concentration of constituents within the biological tissue structure according to the determined resonant frequency and the associated characteristics of the measured response.

The signal processor may be arranged to measure the magnitude response of the ratio of the received microwave energy to the transmitted microwave energy and determine the frequency at which a minima or maxima in the magnitude response occurs, said frequency being the resonant frequency. The signal processor may additionally be arranged to determine the 3 dB bandwidth of the magnitude response for the frequency of the minima or maxima and thereby derive the Q factor of the biological tissue structure. The data processor may additionally be arranged to correlate the derived value of Q factor to a constituent concentration value. The data processor may be additionally arranged to determine other characteristics such as slope or gradient of the measured data.

The signal processor may be further arranged to measure the phase response of the ratio of the received microwave energy to the transmitted microwave energy and determine the frequency at which a minima or maxima in the phase response occurs, said frequency being the resonant frequency.

The first and second antennas may comprise a single transceiver wherein the received microwave energy comprises reflected microwave energy. Preferably, a reflector plate is arranged to reflect microwave energy transmitted from the single antenna back to said transceiver. In this arrangement, a resonant cavity is set-up between the antenna and the plate.

The microwave energy source may be arranged to generate microwave energy over a range of frequencies such that at the resonant frequency the biological tissue structure forms a single wave resonant cavity.

Preferably, the microwave energy source is arranged to generate microwave energy over a range of frequencies such that at the resonant frequency the biological tissue structure forms a half wave resonant cavity.

More preferably, the microwave source is arranged to generate microwave energy within the frequency range of 1 GHz to 100 GHz. Even more preferably, over the frequency range of between 8 GHz and 18 GHz.

The microwave source may be arranged to generate microwave energy within a number of frequency bandwidths within said frequency range.

The first and second antennas may each comprise a patch antenna, each antenna having a radiating patch and a microwave feed line. The microwave feed line may comprise a micro-strip line connected to the radiating patch, a coaxial feed or the microwave feed line may be electromagnetically coupled to the radiating patch. Additionally, the radiating patch may include an annular slot formed therein.

Alternatively, wherein the first and second antennas comprise spiral or waveguide antennas.

Preferably, the first and second antennas are arranged to be non-invasively attached to the biological tissue structure. Alternatively, the first and second antennas may comprise one of waveguide antennas or coaxial monopole antennas, each antenna having an inner and an outer conductor, where the inner conductor preferably comprises a needle like structure arranged to pierce the surface layer of the biological tissue. Additionally, the outer conductor may be arranged to pierce the surface layer of the biological tissue.

The data processor may be arranged to correlate the determined resonant frequency to the thickness of the biological tissue structure to provide the constituent concentration information. A value for the biological tissue structure thickness may be provided as a predetermined input parameter or alternatively the signal processor may be arranged to measure the capacitance of the biological tissue structure between the first and second antennas, from which the thickness value may be derived. Other methods of measuring the thickness include a resistive method where resistance is proportional to thickness and an optical displacement sensor.

The first and second antennas are preferably arranged to be attached to either side of at least one of an earlobe or the skin interconnecting a thumb and forefinger. Other regions of the anatomy that are rich in blood flow and simple in structure may also be considered.

Preferably, at least the microwave source, and first and second antennas are arranged as a portable assembly for wearing by an individual.

At least one of the signal processor and data processor may comprise one from the list of a personal computer, a laptop computer, a mobile computer, a wrist watch with a microprocessor and a mobile telephone.

The constituent concentration preferably comprises at least blood-glucose, blood-alcohol or cholesterol.

According to a second aspect of the present invention there is provided a method of minimally invasively measuring concentrations of constituents contained within a biological tissue structure, the method comprising generating a range of microwave frequencies, transmitting at least a portion of the generated microwave energy into the tissue structure, receiving at least a portion of the microwave energy transmitted through the tissue structure, determining the resonant frequency of the received microwave energy and providing an output of the concentration of constituents within the biological tissue structure according to the determined resonant frequency and the measured response.

The magnitude response of the ratio of the received microwave energy to the transmitted microwave energy may be measured and the frequency at which a minima or maxima in the magnitude response occurs determined, said frequency being the resonant frequency.

The 3 dB bandwidth of the magnitude response for the frequency of the minima or maxima may be determined and therefore the Q factor of the biological tissue structure is derived. The derived value of Q factor may be correlated to a constituent concentration value.

The phase response of the ratio of the received microwave energy to the transmitted microwave energy may be measured and the frequency at which a minima or maxima in the phase response occurs is determined, said frequency being the resonant frequency.

The microwave energy is preferably generated over a range of frequencies such that at the resonant frequency the biological tissue structure forms either a single or half wave resonant cavity. The microwave energy is preferably generated within the frequency range of 8 GHz to 18 GHz. Additionally, the microwave energy is generated within a number of frequency bandwidths within said frequency range.

The determined resonant frequency may be correlated to the thickness of the biological tissue structure to provide the constituent concentration information. A value for the biological tissue structure thickness may either be provided as a predetermined input parameter or the capacitance of the biological tissue structure may be measured, from which the thickness value maybe derived.

Preferably, the biological tissue structure comprises one of an earlobe or the skin interconnecting a thumb and forefinger and the constituent concentration comprises at least blood-glucose, blood-alcohol or cholesterol.

BRIEF DESCRIPTION OF DRAWINGS

Embodiments of the present invention will now be described, by way of non-limiting examples only, with reference to the accompanying figures, of which.

DETAILED DESCRIPTION OF THE INVENTION

Figure 1:
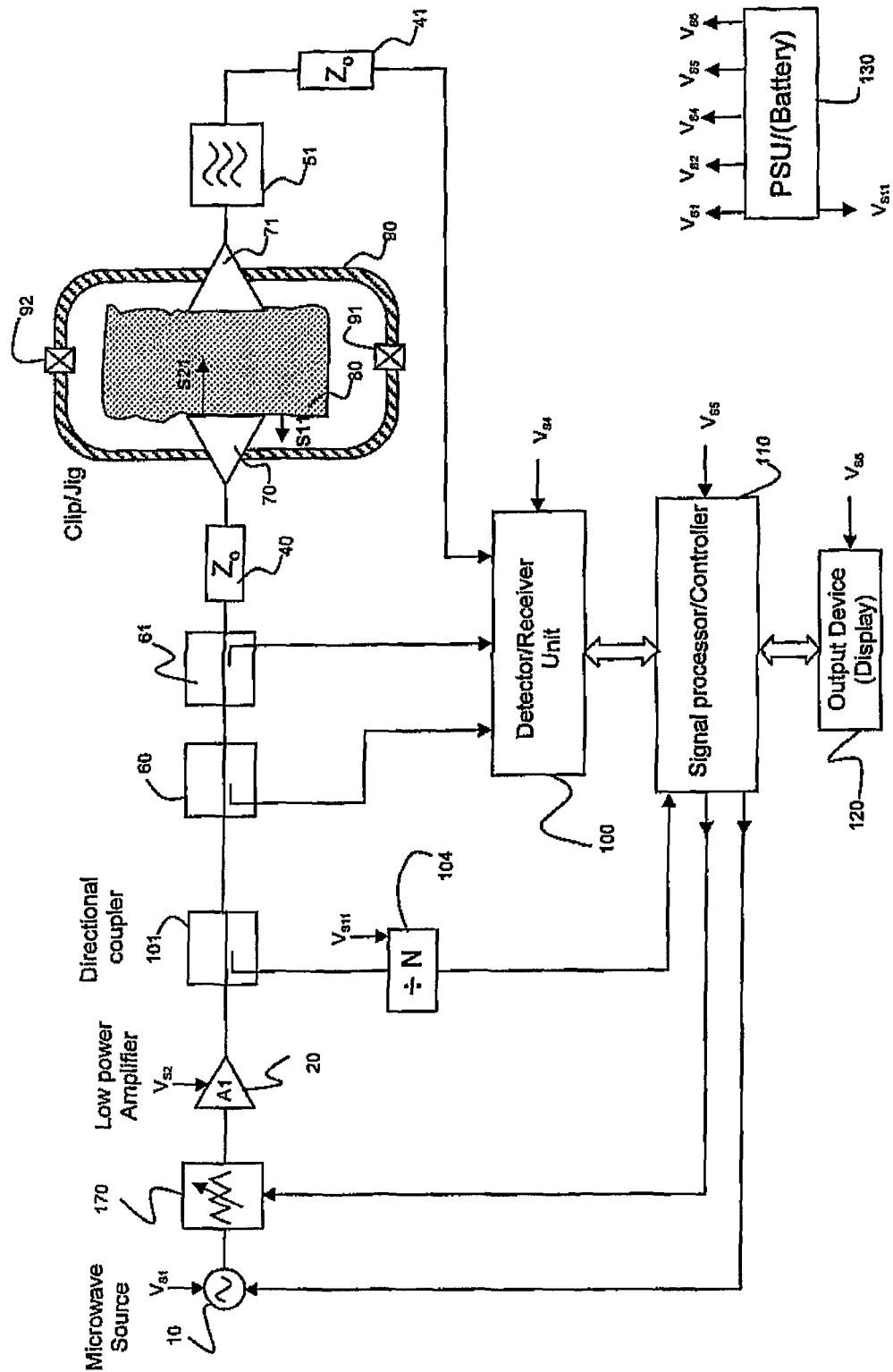
FIG. 1 shows a block diagram of an embodiment of the present invention.

FIG. 1 schematically illustrates apparatus according to a first embodiment of the present invention. A microwave source 10 is connected to a power control device 170, such as a PIN diode attenuator, followed by a low power amplifier 20. The microwave source 10 may be any suitable oscillating device, such as a voltage controlled oscillator (VCO), dielectric resonator oscillator (DRO), surface acoustic wave device (SAW), or frequency synthesiser. The latter will be used in the instance where it is required to sweep the frequency over a large range. A VCO device may be used where the range of frequencies is more limited. Embodiments of the present invention may be used over the microwave frequency range of between 1 GHz and 100 GHz, subject to microwave devices available and physical or geometrical constraints apply. In embodiments of the present invention preferred frequency ranges are 4.45 GHz to 5 GHz (550 MHz sweep range), 5.6 GHz to 6.8 GHz (1.2 GHz sweep range) and 13.2 GHz to 13.5 GHz (300 MHz sweep range). In some embodiments it may be preferred to have a single microwave frequency, or a number of discrete frequencies, in which case it is preferable to phase lock the microwave source.

The output power of the low power amplifier 20 is preferably less that 100 mW when operated in continuous wave (CW) mode, but this may be increased when operated in pulse mode, where the duty cycle can be much lower than 50%, hence the peak power can be greater than 100 mW whilst maintaining an average power of equal to or less than 100 mW. However, other power levels may also be used. The output of the amplifier 20 is connected to the input of a first directional coupler 101, whose coupled port is connected to the input of a frequency divider (pre-scalar) 104. The orientation of first directional coupler 101 is such that forward power from amplifier 20 will enter the coupled port. The output from 101 is connected to the input of a second directional coupler 60, whose coupled port is connected to a detector/receiver unit 100. The orientation of the second directional coupler 60 is such that forward power from amplifier 20 will enter the coupled port. The output from the second directional coupler 60 is connected to the input of a third directional coupler 61, whose coupled port is also connected to the detector/receiver unit 100. The orientation of the third directional coupler 61 is such that reflected power will enter the coupled port. The output from 61 is connected to the input of a co-axial cable assembly 40, and the distal end of cable assembly 40 is connected to a first antenna 70, which is used to transmit microwave energy from microwave source 10, and low power amplifier 20, into a portion of a biological tissue structure 80. In practice, cable assembly 40 may not be required, as in certain embodiments coupler 61 is connected directly to first antenna 70. A second antenna 71 is connected to a matching filter 51, whose function is to provide an impedance match between the output of the second antenna 71 and the surface of the biological tissue structure 80 to enable maximum power transfer into the tissue, which will lead to the highest possible signal strength and ensure that the signal fed into the detector 100 is above the noise floor of said detector 100. The output from the matching filter 51 is connected to the input of a co-axial cable assembly 41, and the distal end of the co-axial cable 41 is connected to a third input of the detector/receiver unit 100. In practice, the cable assembly 41 may not be required, as in certain embodiments the detector/receiver unit 100 will be connected directly to the second antenna 71. The matching filter 51 may be excluded from the line up in the instance where it is not required to match the energy to the tissue or where said the second antenna 71 has been statically matched to the surface of said biological tissue structure 80 during manufacture. On the other hand, a second matching filter may also be required to transfer energy more efficiently from the microwave source 10 and low power amplifier 20 into the biological tissue structure 80. The first and second antennas 70,71 are preferably fixed to the biological tissue structure 80 and are aligned using a clip arrangement 90 and fasteners 91,92. The biological tissue structure is preferably the earlobe or the web of the hand between the thumb and first finger, but this invention is not limited to using these regions of the human biological system.

The output from the frequency divider (pre-scalar) 104 provides a first input into the signal processor/controller 110, where the output frequency produced by the microwave source 10 is identified and stored in an internal memory. The coupled signals from the second and third couplers 60,61 provide information regarding the forward transmitted and forward reflected signals, and the signal from the distal end of the second co-axial cable-assembly 41 provides information regarding the forward received energy after the microwave energy has passed through the biological tissue structure 80. The difference in phase and/or magnitude between the energy impinging on the second antenna 71 and that transmitted from the first antenna 70 provides information regarding the concentration of constituents contained within the biological fluid (normally blood). The signals from the couplers 60 and 61, and the forward received signal are also fed into the detector/receiver unit 100, where phase and magnitude information is extracted and also fed into the signal processor/controller 110. The phase and magnitude information is correlated with the frequency information supplied by the frequency divider (pre-scalar) 104 using the signal processor/controller 110 and changes in phase and/or magnitude are calculated.

The signal processor/controller 110 is also arranged to send a control signal to PIN attenuator 170 to control the microwave power level and to send a control signal to the microwave source 10 to enable the output frequency to be swept. The signal processor/controller 110 also performs noise filtering, signal conditioning and performs any other desired signal processing and monitoring functions in a manner known to the person skilled in the art.

The processed information is fed into a suitable output device 120, which presents patient information, provides the necessary user control facilities and acts as an interface to the outside world.

In embodiments of the present invention it is desired to create a resonant microwave cavity within the tissue structures between the two antennas. In preferred embodiments the distance between the antennas is approximately 3.5-3.7 mm, as dictated by the thickness of the tissue, which means that this needs to be a length of a single wavelength, for example, of microwave energy for resonance to occur (it will be appreciated that resonance may occur at other integers or fractions of wavelengths, such as a half wavelength). This measurement approximately matches the thickness of skin found between the thumb and forefinger or the thickness of the earlobe. Given the wavelength, the required frequency for resonance is dictated by the permeability of the medium through which the microwave energy travels. Consequently, if the frequency of transmitted microwaves is swept over a frequency range encompassing the resonant frequency for the given permeability of the transmission medium, then the received energy will display either a minimum or a maximum in its magnitude at the resonant frequency (depending on the method of detection, the material within the cavity and the cavity itself). However, if the permeability of the transmission medium alters, the resonant frequency will change. It is this characteristic that embodiments of the present invention utilise, since the permittivity of the tissue varies with the concentration of blood-glucose. The phase of the microwave energy either received by a second antenna or reflected back to the first antenna relative to the transmitted microwave energy is also dependant on the permittivity of the transmission medium and hence on the blood-glucose concentration in the tissue structures. This characteristic is also utilised in embodiments of the present invention.

The directional couplers 101,60,61 are preferably fabricated onto a microwave dielectric substrate with copper, or another suitable metallic coating, on both sides. The preferred arrangement for the couplers is edge-coupled microstrip lines, although other microwave directional couplers will be apparent to the skilled person. The main constraints associated with the choice of couplers are the need for high directivity and the limitations on size due to the requirement to integrate the instrument into a small package.

Figure 2:
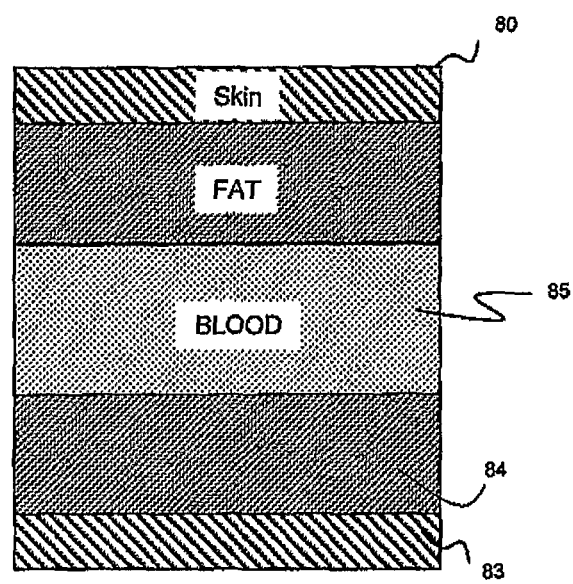
FIG. 2 schematically illustrates a typical biological structure used with embodiments of the present invention.

As mentioned above, the preferred locations of the human anatomy for the measurements to be carried out are the earlobe and the web of the hand between the thumb and the first finger, since these regions are rich in blood flow and are biologically simple in structure. Ideally, the layers of tissue sandwiched between the antennas 70,71, except the blood itself, will exhibit a constant value of conductance and relative permittivity. An illustration of a typical biological structure used with the instrument is shown in FIG. 2, where it is assumed that the structure is symmetrical and consists of only three tissue types; namely: skin 83, fat 84 and blood 85. Of course, the structure will also contain water. The thickness of the overall structure varies from between about 2 mm and 20 mm, thus the propagation loss will be low. For example, using a first order approximation, signal attenuation at a frequency of 10 GHz will be as follows: blood=−1.5 dB/mm, dry skin=−1.13 dB/mm and fat=−0.22 dB/mm.

Figure 3:
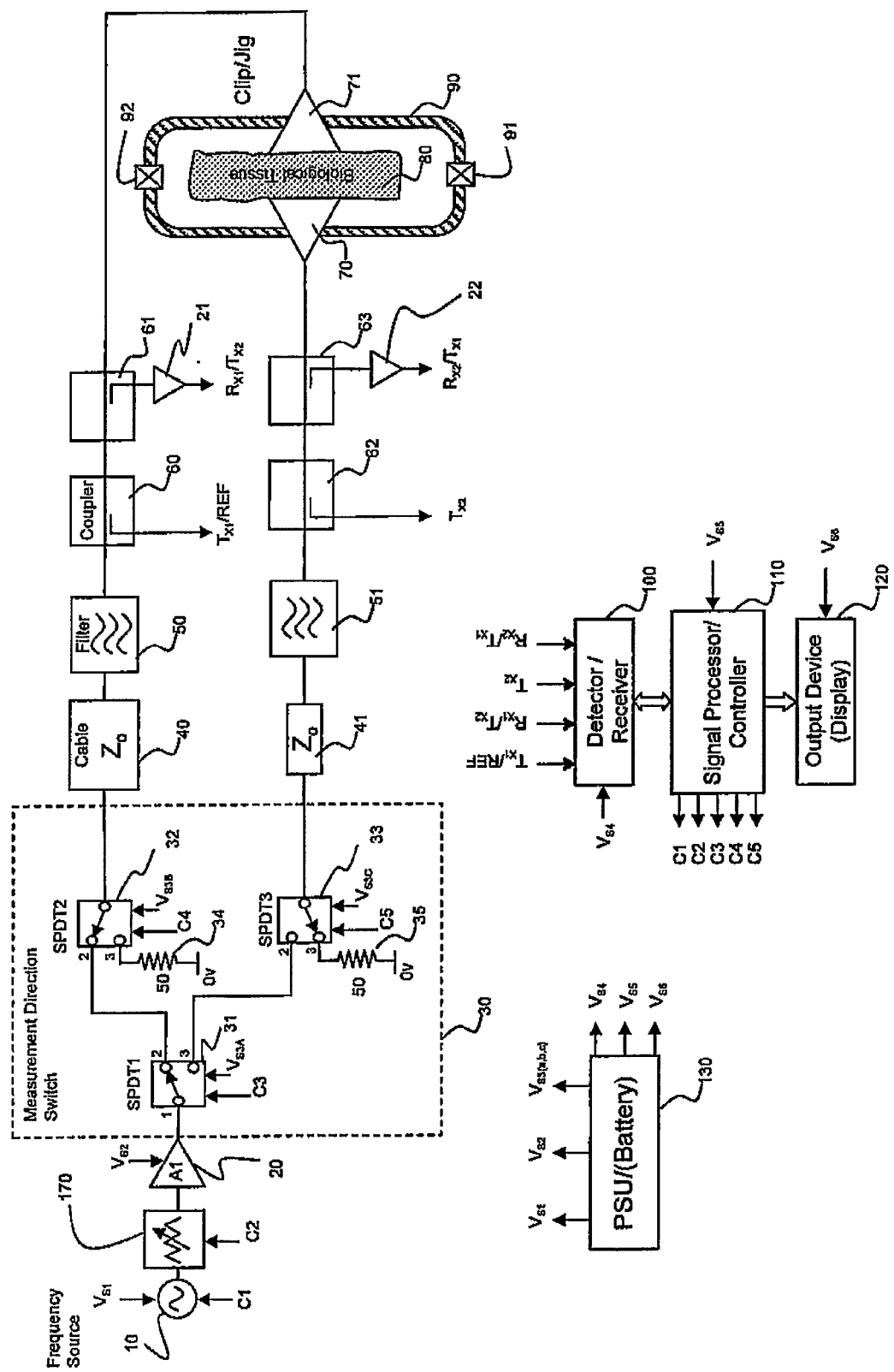
FIG. 3 shows an embodiment of the present invention to measure transmission and reflection characteristics in two directions.

In certain instances it may be preferable to perform measurements in two directions using a single microwave source 10. FIG. 3 shows an embodiment of the present invention to enable full two port measurements to be made. The measurements could be a combination, or all of, the following: transmission from first antenna 70 through biological tissue 80 to second antenna 71, reflection from biological tissue 80 back to first antenna 70, transmission from second antenna 71 through biological tissue 80 to first antenna 70, and reflection from biological tissue 80 back to second antenna 71. An arrangement of electronically controllable switches 30 is used to enable measurement direction change over to take place automatically.

In the configuration shown in FIG. 3, three single-pole-two-throw (SPDT) switches are used to enable the microwave line-up 10, 170, 20 to be used as a microwave energy source for both first antenna 70 and second antenna 71. In a first configuration, as shown in FIG. 3, a first electronic switch SPDT1 31 provides the microwave energy from the amplifier 20 to a second electronic switch SPDT2 32, which in turn provides the microwave energy to the input of a transmission line 40, whose output is connected to the input of a first matching filter 50. The output from said first matching filter 50 is fed into the input of a first directional coupler 60, which is configured as a forward power coupler in an analogous manner to the arrangement shown in FIG. 1, and whose coupled port is fed directly into the detector/receiver unit 100. The output from the first coupler 60 is fed into the input to second directional coupler 61, which in the illustrated configuration is configured as a reverse power coupler and is used to measure reflected forward power from the biological tissue structure 80. A signal booster amplifier 21 is shown connected to the coupled port of second coupler 61. This amplifier 21 is used to increase the signal strength in the instance where the loss through tissue structure 80 is high or the strength of the signal produced by the microwave line-up 10,170,20 is inadequate. The output from amplifier 21 is fed into the detector/receiver unit 100.

In the illustrated configuration, a third electronic switch SPDT3 33 is connected between ground through a 50Ω resistor 35 and the input of a further transmission line 41, whose output is connected to the input of a second matching filter 51 (N.B. in this switch configuration 51 is connected, but is not used). The output from first matching filter 51 is fed into the input of a third directional coupler 62, which is configured as a forward power coupler and whose coupled port is fed directly into detector/receiver unit 100 (N.B. in this switch configuration third directional coupler 62 is not used). The output from the third coupler 62 is fed into the input of a fourth directional coupler 63, which is configured as a reverse power coupler and in the illustrated configuration is used to measure transmitted power from the second antenna 71 after being transmitted through biological tissue structure 80. A second signal booster amplifier 22 is shown connected to the coupled port of the fourth directional coupler 63 and is provided for the same reasons as the first booster amplifier 21. The output from the second amplifier 22 is fed into the detector/receiver unit 100. In this configuration the microwave energy is transmitted by the first antenna 71 and received by the first antenna 72.

A second configuration for electronic switches SPDT1 31, SPDT2 32 and SPDT3 33 enables the microwave energy to be transmitted by the first antenna 70 and received by the second antenna 71. In the second configuration the first switch 31 is connected to the third switch 33 to provide the output of the amplifier 20 to the second transmission line 41, the third switch 33 no longer being connected to ground. The second switch now connects the first transmission line 40 to ground via a 50 ohm resistor 34. In this second configuration third coupler 62 measures the transmitted microwave energy, fourth coupler 63 measures the energy reflected back from the first antenna 70 and second coupler 61 measures the received microwave energy. First coupler 60 is not used in this configuration.

The position of the switch contacts is controlled using control signals generated by signal processor/controller 110. The electronic switches 31, 32, 33 are preferably micro-electro-mechanical systems (MEMS) based devices, PIN diode based devices (reflective or absorptive) or metal oxide semiconductor (MOS) devices, although other types of electronic switch known to the skilled person may be used. The most suitable device will be somewhat dependent upon the final frequency used.

Figure 4:
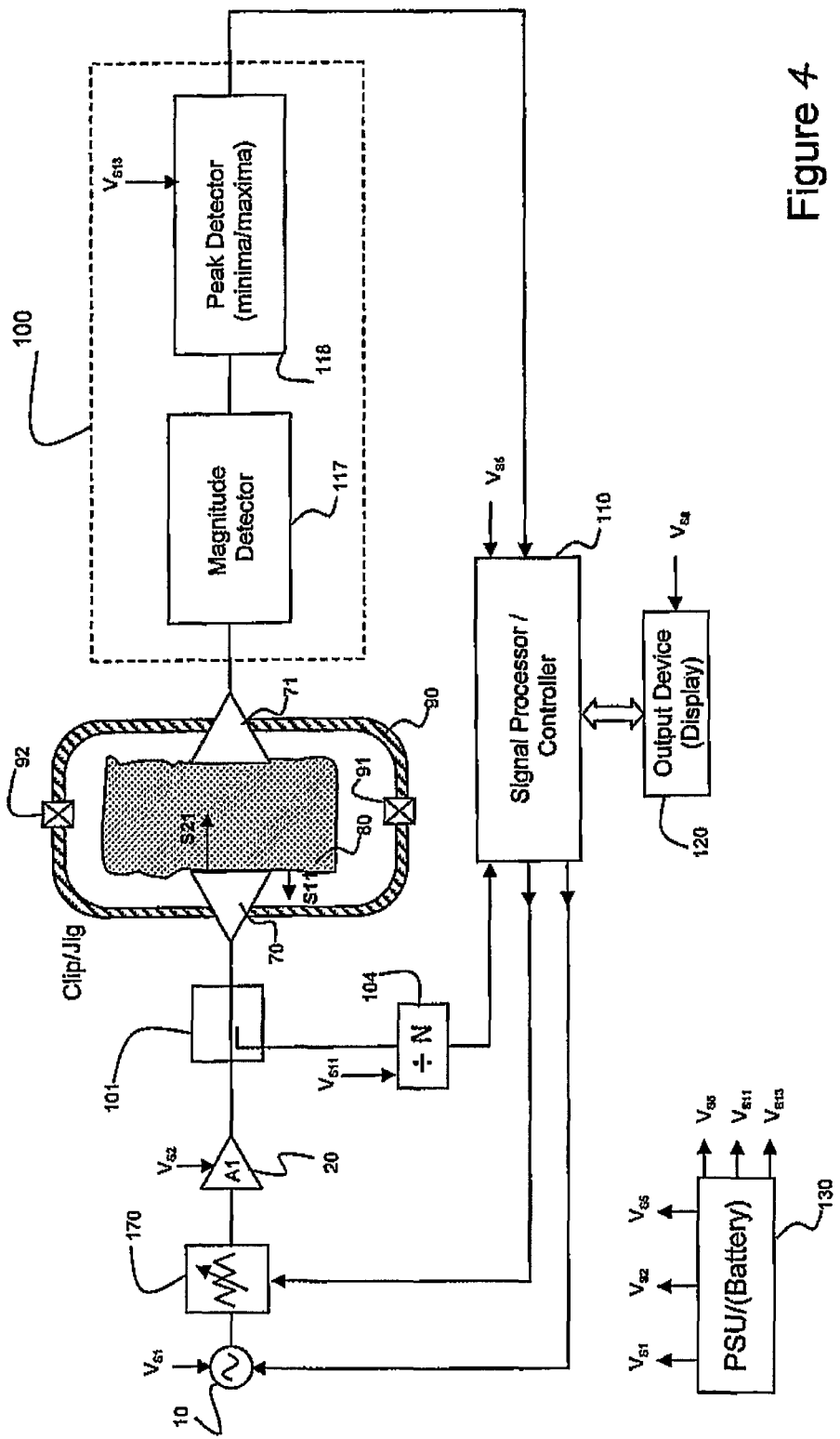
FIG. 4 shows an arrangement for measuring magnitude response.

FIG. 4 shows an embodiment of the present invention for measuring magnitude information only and detects positive or negative peak values (maxima or minima) that occur in the magnitude response over a frequency range of interest. As in FIG. 1, a microwave source 10, signal attenuator 170 and low power amplifier 20 are provided, although in this embodiment the microwave source 10 is either a frequency synthesiser or a VCO, whose output frequency can be swept over the range of interest by applying a control voltage at the input. The frequency is monitored using directional coupler 104, arranged such that the coupled port measures a portion of forward directed power, and said coupled portion of forward power is fed into a divider or frequency pre-scalar 104 to provide a frequency that can be processed by a signal processor/controller 110. The microwave energy signal is transmitted through the biological tissue structure 80 using first antenna 70 and, after propagation through said tissue structure 80, the signal is received at second antenna 71. A magnitude detector 117 is used to detect the signal and a peak detector 118 is used to detected the positive, or negative, going peak. The combination of magnitude detector 117 and the peak detector 118 forms the detector/receiver unit 100. The detected signal from the detector/receiver unit 100 is then fed into the signal processor/controller 110 where it is correlated with said frequency information provided by the frequency divider 104. The magnitude detector may take the form of a diode detector with appropriate filtering, or a homodyne detector, which may use a mixer and a local oscillator. Other types of magnitude detectors will be known to a person skilled in the art. The processor/controller 110 is used to determine the blood-glucose concentration from said amplitude peak and corresponding frequency information. Said processor/controller 110 also sends information to output device 120 whose function is to display the blood-glucose level in a user-friendly format.

Figure 5:
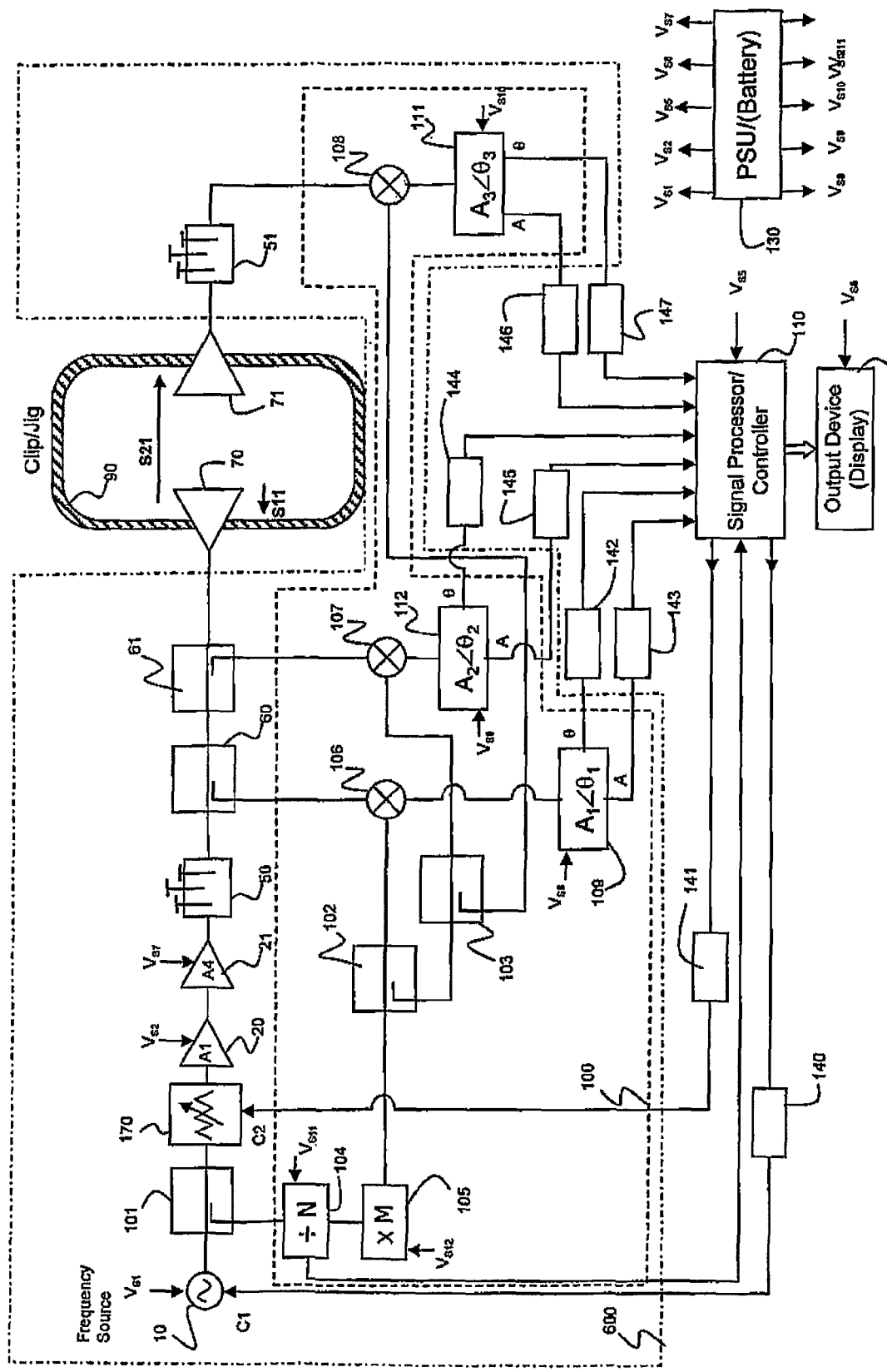
FIG. 5 shows a detailed arrangement of an embodiment of the present invention.

FIG. 5 shows a specific embodiment of the present invention to enable both phase and magnitude information to be measured. In this embodiment frequency mixers are used and operated such that the local oscillator input frequency is different from that of the RF input frequency. This provides two frequencies at the output of said mixer; the sum of the local oscillator frequency and the RF frequency and the difference between the RF frequency and the local oscillator frequency. In this embodiment said local oscillator frequency is derived from the microwave source 10. A portion of the signal from said microwave source 10 is made available using a first directional coupler 101 which is configured with its coupled port arranged to measure a portion of the forward signal produced by the microwave source 10. The coupled power from the first directional coupler 101 is fed into frequency divider (pre-scalar) 104, where the frequency generated by the microwave source 10 is divided by a fixed value (normally an integer) and is then multiplied by a fixed value (normally an integer) to provide a higher frequency using a frequency multiplier 105. The scaled frequency output signal from the frequency multiplier 105 is fed into a second directional coupler 102 and the output of the second directional coupler 102 is fed into the first input, the local oscillator input, of a first mixer 106. The second input to the first mixer 106, the RF input, is taken from the coupled port of a third directional coupler 60, which is configured to measure a portion of the forward directed power being transmitted. The output from first frequency mixer 106 is fed into a first integrated phase/magnitude detector 109, which may be any commercially available packaged phase/magnitude demodulator. The phase/magnitude information produced by the phase/magnitude detector 109 is fed into the signal processor/controller 110.

The scaled reference frequency taken from the output of the frequency multiplier 105 is also used as the local oscillator frequency inputs for a second and third frequency mixers 107, 108. The first input, the local oscillator input, to the second mixer 107 is taken from the output of a fourth coupler 103, which in turn receives the coupled output of the second coupler 102. The second input, the RF input, going into said second mixer 107 is taken from the coupled port of a fifth directional coupler 61, which is configured to measure a portion of reflected power coming back via first antenna 70 reflected back in the form of backscatter. The output from the second frequency mixer 107 is fed into a second integrated phase/magnitude detector 112. The phase/magnitude information produced by 112 is fed into the signal processor/controller 110. The first input, the local oscillator input, to third mixer 108 is taken from the coupled port of fourth directional coupler 103, whilst the second input, the RF input, to the third mixer 108 is taken from the output of the second antenna 71 via a second matching filter 51, which matches the impedance of the surface of the biological tissue structure 80 with the aperture of second antenna 71. The output from said third frequency mixer 108 is fed into a third integrated phase/magnitude detector 111 and the phase/magnitude information produced is fed into the signal processor/controller 110.

Directional couplers 1, 2 and 4 (101, 102, 103) are preferably 3 dB couplers or 3 dB splitters, and may take the form of microstrip or stripline devices. It may be preferable to connect low pass filters at the outputs of frequency mixers 106, 107, 108 to ensure that only the difference frequency (RF– Local oscillator frequency) passes into phase/magnitude detectors 109, 112 and 111 respectively and that the sum frequencies produced by said frequency mixers 106, 107 and 108 are rejected. In this embodiment two low power amplifiers 20,21 are used to amplify the microwave signal produced by microwave signal source 10, and first matching filter 50 is used to provide a static impedance match between first antenna 70 and the surface of the biological tissue structure 80.

Figure 6:
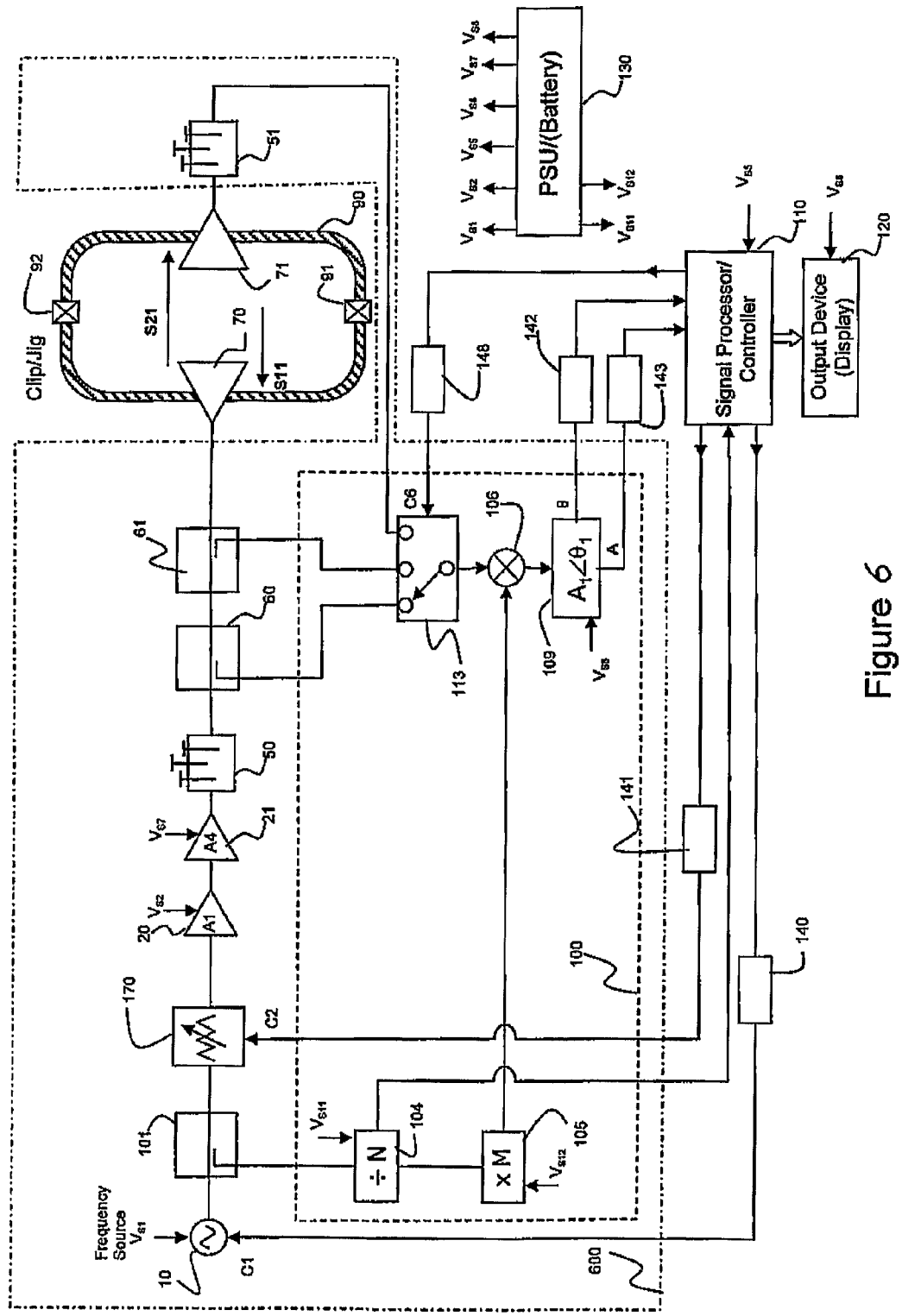
FIG. 6 shows an alternative arrangement to that shown in FIG. 5.

An embodiment similar to that shown in FIG. 5 is given in FIG. 6. This embodiment is similar to the embodiment shown in FIG. 5 and described above except that in this instance the three frequency mixers 106, 107, 108 and the three phase/magnitude detectors 109, 111, 112 are replaced by an electronically controlled single-pole-three-throw switch (SP3T) 113, a single mixer 106, and a single integrated phase/magnitude detector 109. The advantage of this arrangement is that the noise produced by, or injected into, frequency mixer 106 and phase/magnitude detector 109 is common to all phase/magnitude measurements taken from coupled ports of third and fifth couplers 60, 61 and second matching filter 51, thus said noise signals can be subtracted from measurement signals. The output from the coupled port of third directional coupler 60 is connected to the first switch position of the electronic switch 113. The third coupler may be used to measure the level of forward energy that is being transferred into biological tissue structure 80, or may be used as a reference to enable a comparison to be made between the value of phase and magnitude information measured at this position and that measured at other locations. The output from the coupled port of fifth directional coupler 61 is connected to the second switch position of the electronic switch 113 and the output from second matching filter 51 is connected to the third switch position of the electronic switch 113. A control signal C6 is used to change the contact position between the switch positions of the electronic switch 113. The signal processor/controller 110 is used to determine the contact position. The common output from the electronic switch 113 is connected to the second input, the RF input, of the single frequency mixer 106. The second input, the intermediate frequency, to frequency mixer 106 is derived from frequency source 10 in a similar manner to that discussed for the embodiment shown in FIG. 5, although the output from frequency multiplier 105 is fed directly into the first input, the local oscillator input, of the frequency mixer 106. Said frequency mixer 106 produces two frequencies; the sum and the difference, but only the difference is if interest in this embodiment of the current invention. It may be preferable to insert a low pass filter at the output of said mixer 106 to filter out the sum frequency signal, but it is generally the case that devices connected to the output of said frequency mixer 106 will not see the sum frequency due to the fact that the local oscillator and the RF frequency are high microwave frequencies, where high microwave frequency is defined here as being above 10 GHz in this instance. The output from said mixer 106, the intermediate frequency output signal, is connected to an integrated phase/magnitude detector 109 and the phase and magnitude information output signals are connected to the signal processor/controller 110. Preferably the insertion loss of the channel between the input and output should be as low as possible and the level of isolation between the switch contacts should be as high as possible at the frequency of interest.

In preferred embodiments the microwave components are integrated into a device compact that is enough to be carried on a user's person, with the antennas either integrated into the same device or coupled to the device by wired or wireless means. The detector/receiver unit, signal processor and output device, or any combination thereof, may also be integrated into the same package as the microwave components or may be packaged separately with appropriate signal communication means provided to the microwave components. Transmission of the microwave energy, where required, may be by co-axial via, co-axial cable, flexible waveguide or other suitable medium known to the skilled person. Transmission of the control and/or measurement signals may be by either known wired or wireless techniques.

In wireless embodiments of the present invention the integrated microwave assembly may take the form of a stand-alone device, but more preferably are integrated into a commercially available device in order to provide the facility for non-obtrusive blood-glucose monitoring. Such devices may include Bluetooth™ mobile telephone headsets, headphones, hearing aids or a standard earphone. The detector/receiver unit, signal processor/controller and output device are preferably integrated into a suitable wireless device, such as a personal computer (PDA) that may be a stand alone device or integrated within a mobile telephone, a laptop computer or a wrist watch that contains a microprocessor. The use of said personal computer will enable information concerning, for example, blood-glucose level, to be displayed in the form of a numerical value, for example, in mmol/L or mg/dL, or provide a graph of blood-glucose level against time. Preferably the wireless device is arranged to generate an audible warning to advise the user that their blood-glucose level is outside a range deemed to be acceptable and that corrective action is required. Alternatively, the measurement information may be sent to a remote monitoring station that is arranged to process said information and display said information for a doctor, or other qualified person, to monitor the patient's blood-glucose level. Said information may be logged. The sent data may have been processed by the wireless device or may be unprocessed, in which case the signal processor/controller may be provided at the remote location.

Antenna structures 70, 71 suitable for use in the current invention will now be considered. There are a number of features that are preferred for said antenna structures to be appropriate for use in embodiments of the current invention and these are listed below:

It is preferable for said antenna structure(s) 70, 71 to be flexible and manufactured to be conformal with the biological tissue structure 80;

It is preferable for the surface of said antenna(s) 70, 71 to be in direct contact with the surface of said biological structure 80 and for said surface of antenna(s) 70, 71 to be coated with a biocompatible material;

It is preferable for the antenna feed line(s) 128, 129 to be located on a surface within the antenna structure that is not the same as the antenna aperture or the radiating surface;

It is preferable for the feed line(s) 128, 129 to be impedance matched to the input impedance of said antenna(s) 70,71 to prevent reflections occurring at said feed point;

It may be preferable for said antenna(s) 70,71 to radiate microwave energy at a single spot frequency that capture the resonant responses and a shift thereof caused by changes in concentration of constituents;

It may be preferable for said antenna(s) 70, 71 to be capable of radiating microwave energy over a band of microwave frequencies;

It may be preferable for said antenna(s) 70, 71 to be capable of radiating microwave energy at a plurality of spot frequencies;

It may be preferable for the radiating elements of said antenna(s) 70, 71 to be impedance matched to the surface of the biological tissue;

It may be preferable for the radiating elements of said antenna(s) 70, 71 to be impedance matched with biological tissue contained within the tissue structure used for the measurements;

It may be preferable for said antenna(s) 70, 71 to radiate microwave energy at a plurality of microwave frequencies and each of the said microwave frequencies to have a finite bandwidth and the said frequencies to be spaced far enough apart to ensure that band overlapping cannot occur;

It is preferable for the surface area of said antenna(s) 70, 71 to be small enough to enable a pair of said antennas, or a single antenna and a reflective plate, to be attached to the human anatomy in a region where the volume of biological tissue structure 80 available for attachment to be made is limited, for example, the earlobe or the web of the hand between the first finger and the thumb;

It is preferable for the structure of said antenna(s) 70, 71 to be non-obtrusive;

It may be preferable for the radiation pattern produced by said antenna(s) 70, 71 to have a high directivity;

It is preferable for said antenna(s) 70, 71 to provide a gain with respect to an isotropic radiator of greater than 0 dBi;

Antenna structures found to be appropriate for use in this invention include: patch antennas, spiral antennas, loaded/unloaded waveguide antennas and radiating slot antennas. Other antenna structures may also be suitable for use in certain applications of the current invention and these will be known to a person experienced in the art of antenna/microwave engineering.

Figure 7:
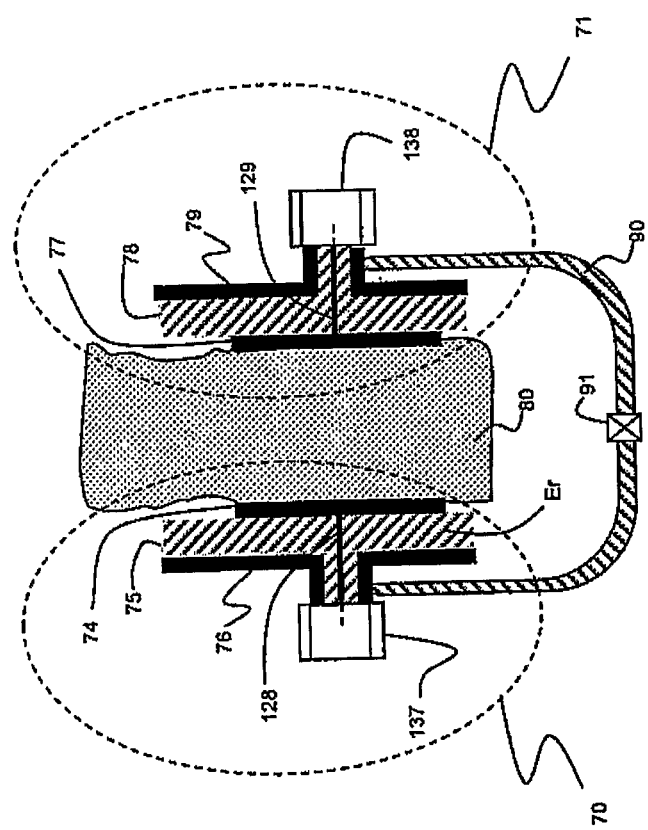
FIG. 7 shows an antenna arrangement according to embodiments of the present invention with two co-axially fed patch antennas.
Figure 8:
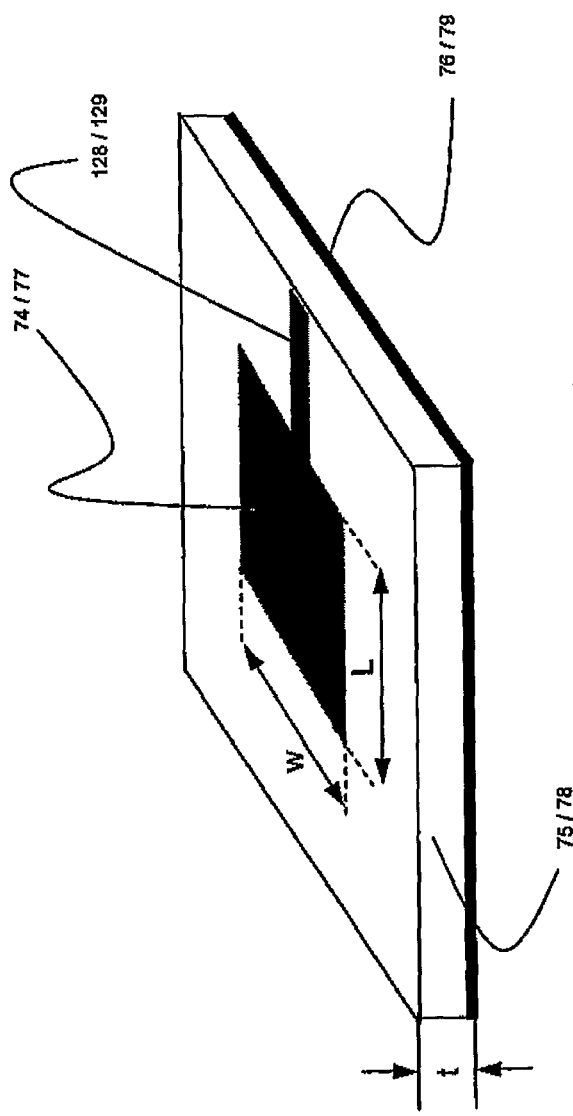
FIG. 8 shows the top view of a rectangular patch antenna fed using a micro-strip line laid on the same plane as the radiating patch.

FIG. 7 shows biological tissue structure 80 sandwiched between a pair of patch antenna 70,71 with clip 90 and fastener 91 used to ensure alignment between said antenna pair 70,71 and to attach said antenna pair 70,71 to the human anatomy. The first antenna assembly 70 and the second antenna assembly 71 are identical, and comprise: a radiating patch 74, 77, a coaxial feed 128, 129, a dielectric material or substrate 75, 78, a ground plane 76, 79, and a co-axial connector 137, 138. Said co-axial connector may take a number of forms, for example, sub-miniature A (SMA), SMB or SMC or another miniature microwave connector that is capable of working at the frequency(ies) of operation relevant to this invention. The arrangement shown in FIG. 7 enables both transmission and reflection (backscatter) measurements to be performed. In further embodiments the second antenna 71 may be replaced by a reflecting plate, in which case reflection (backscatter) only can be measured. The construction of a rectangular patch antenna consisting of a single patch is shown in FIG. 8, where the microwave energy is launched into the radiating patch 74, 77 using a microstrip feed line 128, 129 that is fabricated on the same surface 75, 78 as said radiating patch 74, 77. Said surface 75, 78 is a substrate material that may consist of a relative permittivity (dielectric loading constant) and/or a relative permeability (magnetic loading constant) of greater than unity, which is used to shrink the size of said radiating patch 74, 77. A ground plane 76, 79 is attached to the underside of substrate material 75, 78. It is preferable for the area of said ground plane 75/78 to be greater than the area of said radiating patch 74, 77. Dimensions that are of importance to ensure efficient energy propagation from said radiation patch 75, 77 are: patch width (W), patch length (L) and substrate thickness (t); these dimensions are indicated in FIG. 8. It is preferable for W to be comparable to the wavelength at the desired frequency of operation in order to enhance the radiation emitted from the edges of said radiating patch 74, 77. For the fundamental $TM_{10}$ mode to propagate, the length L should be slightly less than $\lambda/2$, where $\lambda$ is the wavelength in substrate material 75, 78.

If the patches are considered as cavity resonators (boxes) with four out of the eight sides missing then the radiation from said patch antennas 70, 71 is the result of energy leaking out of the resonant cavities (radiation is primarily due to energy leaking from the two gaps of width W). As stated previously, the thickness t of the substrates 75, 78 is typically small relative to the other dimensions of said patches 74, 77 therefore the energy leaking out of the boxes is much smaller than the energy stored within it. In order to achieve wide bandwidth operation, it is necessary to use the substrate material 75, 78 with the highest thickness t and lowest relative permittivity $\in_r$ (this assumes only dielectric loading) that is practically possible. These requirements of course may conflict with the requirement to make the patch size as small as possible and also provide a matched feed line. Possible candidates for substrate material 75, 78 are as follows: semi-insulating GaAs ($\in_r=13$), silicon ($\in_r=11.9$, PTFE-ceramic, composite ($\in_r=10.2$), silicon resin-ceramic ($\in_r=3$ to 25) and Ferrite ($\in_r=9$ to 16). Materials for the radiating patches 74, 77, the ground-planes 76, 79 and the feed lines 128, 129 may include, but is not limited to: copper, brass, silver, silver platted copper and aluminium. It may be desirable to cover said radiating patch with an insulating material and it may be preferable for said insulating material to be biocompatible. Said insulating cover will affect the performance of said antennas 70, 71 and so the effect of including said cover must be considered. A dielectric cover will cause the resonant frequency of the patch antenna 70, 71 ($f_o$) to be lowered, therefore the antenna structure without the cover must be designed to resonate at a slightly higher frequency than the desired operating frequency, or the frequency at the centre of the band of operating frequencies. In general, when said patches 74, 77 are covered with a dielectric, the following properties will change: $\in_{r\ eff}$, losses, Q-factor and directive gain. The change in $\in_{r\ eff}$ causes the greatest change and the amount of change is dependent upon the thickness t and the relative permittivity $\in_r$ of the substrate. The presence of said cover also produces a change in the near/far field radiation patterns.

In designing the most appropriate antenna construction, it is preferable for the feed lines 128, 129 not to be on the same surface as the radiating patches 74, 77 due to the fact that said feed lines 128, 129 will also radiate energy into the biological tissue structure 80 and reduce the effectiveness of the antennas radiating into the tissue. This factor becomes most important when the instrument is operated at high microwave frequencies and high values of relative permittivity and/or relative permeability are used as the substrate material 75, 78, due to these factors causing the radiating patches 74, 77 to become very small. FIG. 26 illustrates an alternative form of antenna feed, the co-axial feed. In this arrangement, the centre conductor of the coaxial connector forms feed lines 128, 129 and said feed lines 128, 129 are soldered to the radiating patches 74, 77. The main advantage of this feed system is that the position of the feed-point determines the input impedance of the patch 74, 77 and so the feed-point can be simply moved around t0 adjust said input impedance. The disadvantages are that a hole has to be drilled in the substrate 75, 78 and the connector protrudes outside the bottom of the ground plane 76, 79, thus the structure is not completely coplanar. Also, to achieve wide bandwidth operation, a thick substrate 75, 78 is required and so the probe (or pin) length becomes longer, which can give rise to increased spurious radiation emission from the probe, increased surface wave power, and increased feed inductance. However, the feed inductance can be compensated for using, for example, a series connected capacitor. One approach used to introduce said series capacitor is to etch out an annular slot in the patch metallization concentric with the probe. All other parameters are the same as those discussed with reference to FIG. 8. FIG. 27 shows an alternative feed arrangement whereby the feed line 128, 129 is electromagnetically (or capacitively) coupled to the radiating patch 74, 77. In this arrangement the substrate layer 75, 78 is made up of two separate dielectric (and/or magnetic) materials and said materials may have different values of relative permittivity (and/or relative permeability). Said feed line 128, 129 is sandwiched between said substrate layers 75, 78, which are themselves placed between said radiating patch 74, 77 and ground plane 76, 79. This method of coupling microwave energy into the radiating patches 74, 77 is also known as proximity coupling and the advantage of this feed configuration is that spurious feed-network radiation coupled into the biological tissue structure 80 is eliminated. Careful choice of the two different relative permittivity values for the substrate material 75, 78 (one for the patch 74, 77 and one for the feed line 128, 129) can be used to optimise the overall performance of the antenna 70, 71. The increased overall thickness of the substrate 75, 78, and the fact that two dielectric materials are now in series, can be used to increase the bandwidth of operation. It may be preferable to include a balanced-to-unbalanced (balun) transformer with certain arrangements to match the unbalanced co-axial, or microstrip, feed 128, 129 to the balanced antenna 70, 71.

If a horn antenna or loaded rectangular/cylindrical waveguide antenna structure is used and the physical dimensions are such that is possible to support the dominant $TE_{10}/TE_{11}$ modes of propagation in air, i.e. $\in_r$ is unity, then it is not required to load the antenna structure with a dielectric or magnetic material. On the other hand, if a horn antenna, or a loaded rectangular/cylindrical waveguide antenna structure is used and the physical dimensions are such that is not possible to support the dominant $TE_{10}/TE_{11}$ modes of propagation in air then the antenna must be loaded with a suitable dielectric or magnetic material whose relative permittivity/permeability is greater than unity. The horn antenna structure must be designed to couple well into the surface of the skin, or other biological material that is of interest. This may be achieved by inserting tuning stubs into the broad wall of the antenna feed line.

In further embodiments of the present invention the antennas preferably consist of fine needle structures that can be partially, or, in some instances, fully inserted into the biological tissue. Possibly antenna structures for these embodiments include co-axial and loaded waveguide antennas. For the latter construction, the preferred shape is the cylinder. For the co-axial structure it is preferable to insert only the centre conductor in to the biological tissue. It is also preferable for the outside diameter of the overall co-axial structure to be less than 0.5 mm, and more preferably less than 0.15 mm. It is also preferable for the diameter of the centre conductor of the co-axial structure to be less than 0.2 mm, and more preferably less than 0.05 mm. A further antenna structure that may be preferable for non-invasive measurements is the slotted line antenna structure, where the face of the antenna that is in contact with the skin is a complete ground plane except for a slot that radiates energy into tissue. A dielectric material is connected to the opposite side of the ground plane and a microstrip line is arranged over the slot to enable energy to be coupled into the slot and into tissue. The feed-line is on the same side as the radiating microstrip, thus problems associated with feed line coupling into tissue are overcome. The slotted line antenna may be the antenna of choice.

A typical setup showing an antenna arrangement piercing biological tissue structures to varying depths of penetration is shown in FIG. 3, which shows a first antenna arrangement 60, 74, 75 mounted to the surface of the skin with the needle antenna 74 penetrating through the skin (epidermis and dermis) 83, the fat layer 84, and into blood 85, and a second antenna arrangement 61, 78, 79 is shown connected to the opposite side of the tissue structure where needle antenna 78 also penetrates as far as the region containing blood 85. A similar arrangement may be provided in which the first and second antennas are mounted adjacent to one another on the same side of tissue structure 80. Alternatively, only a single needle antenna may be provided mounted on the surface of the skin 83. In this arrangement the single antenna is used to both transmit microwave energy and measure reflected energy. In all three previous arrangements the needle 74 may be arranged to penetrate into the skin only to the depth of the lower epidermis or the dermis. In the arrangement shown in FIG. 9 the female coaxial connector 75/79 is connected to a biocompatible patch 60/61 and dielectric material is provided between the inner and outer conductors 37/77. The dielectric material 73/77 is flush with the bottom of the biocompatible patch (or pad) 60,61 and the inner conductor needle (or pin) is shown protruding through the bottom of said patch 60/61.

Figure 9:
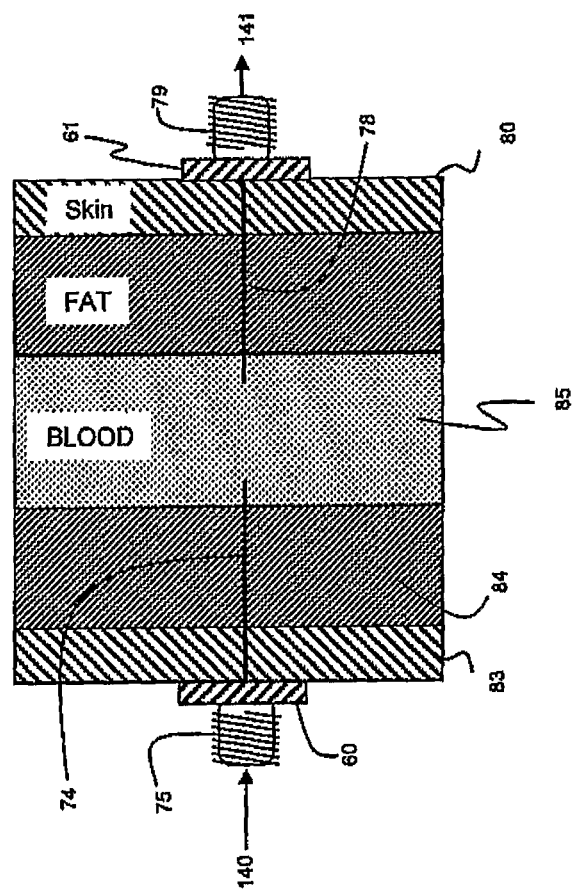
FIG. 9 shows a possible configuration for a pin antennas arranged to penetrate the biological tissue.

In the arrangement shown in FIG. 9 only the centre conductor 78, 74 is arranged to be inserted into the tissue structure(s). However, in other embodiments the antenna may be arranged such that the complete co-axial antenna can be inserted into the tissue. In these co-axial antenna structures it is preferable for the outside diameter of the overall co-axial structure 72/76 to be less than 0.5 mm, and more preferably less than 0.15 mm. It is also preferable for the diameter of the centre conductor 74/78 to be less than 0.2 mm, and more preferably less than 0.05 mm. The length of the portion of the centre conductor to be inserted into the tissue will be dependent upon the dielectric constant of the tissue. In general, the length in free space will be shortened by the inverse of the square root of the relative permittivity of the biological tissue 80. It is preferable to coat the inner conductor 74/78 with a conformal coating of biologically acceptable material. In the instance where the complete co-axial antenna structure is inserted into the biological tissue, a portion of, or, in some cases the complete, co-axial structure may be coated with a biologically compatible material.

Figure 10:
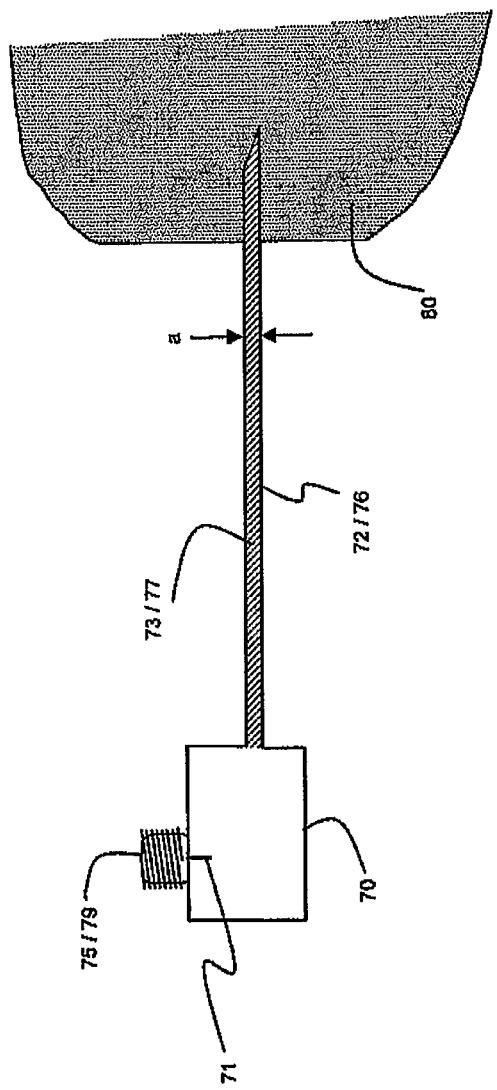
FIG. 10 shows an arrangement for a loaded cylindrical antenna arranged to penetrate the biological tissue.

FIG. 10 shows a dielectric loaded waveguide antenna structure according to further embodiments of the present invention. A cylindrical waveguide is loaded with a material that exhibits a low loss at the frequency of interest, and has a high relative permittivity in order to shrink the diameter of the structure to a value that is acceptable in terms of piercing the skin whilst causing a minimal degree of discomfort. The arrangement shown in FIG. 10 the microwave signal launched into the waveguide probe using an E-field probe 71 connected to a co-axial microwave connector 75/79. In the arrangement shown, a waveguide cavity 70 is used to launch the dominant $TE_{11}$ mode into the waveguide. Ideally, the distance between the E-field probe and the closed back wall of 70 is a quarter wavelength (or an odd multiple thereof) at the frequency of operation.

In some embodiments of the present invention the centre conductor of the antenna shown in FIGS. 9 & 10 may be hollow and in fluid communication with a source of medicament. For example, where the constituent concentration being measured is the blood-glucose level of an individual, the antenna may be connected to a source of insulin. This allows the apparatus of embodiments of the present invention to be used as part of a closed loop system, wherein the medicament, or other desired fluid, can be administered to an individual automatically according to the measured constituent concentration.

Figure 11:
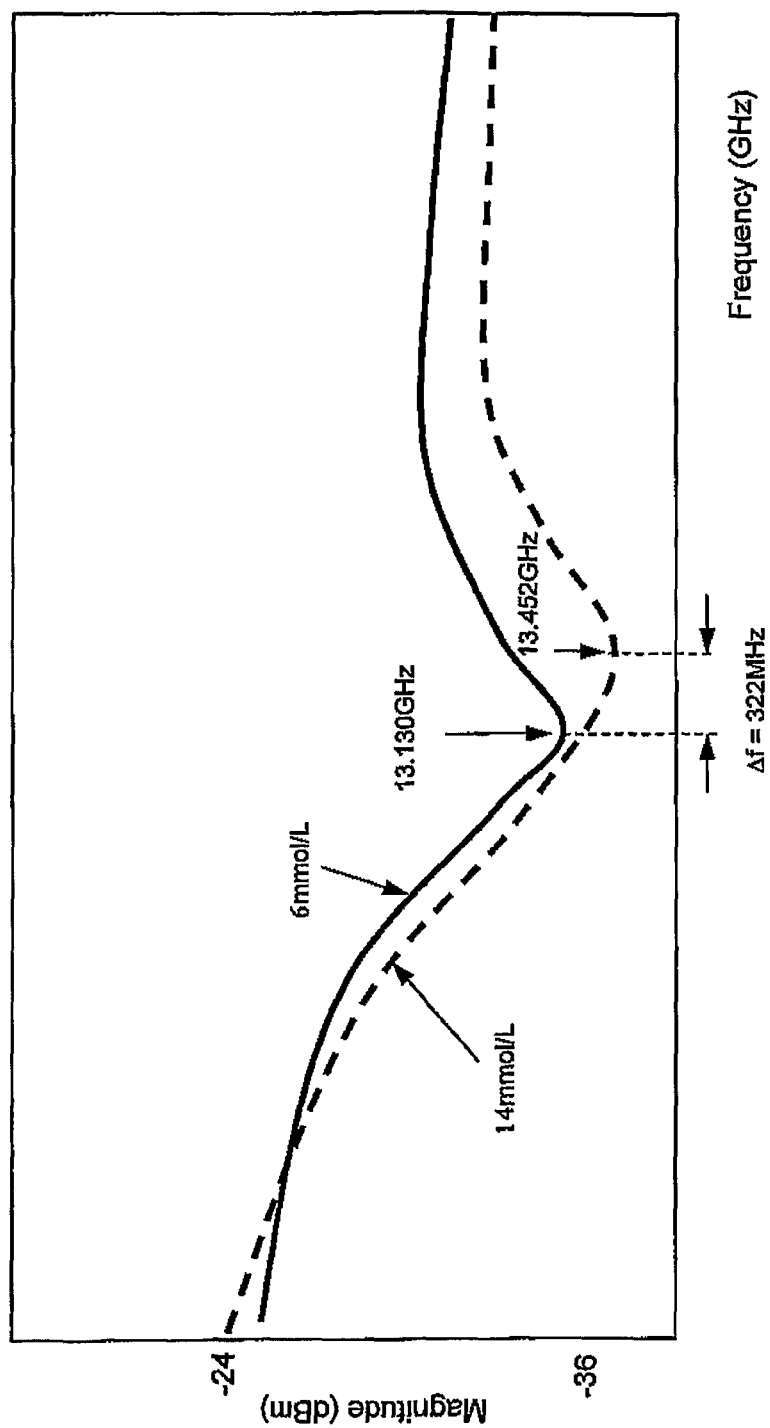
FIG. 11 is a graph showing magnitude change results obtained from apparatus according to embodiments of the present invention.

FIGS. 37 and 38 respectively show the magnitude and phase responses obtained using apparatus according to embodiments of the present invention to investigate two blood-glucose solutions having glucose concentrations of 6 mmol/L and 14 mmol/L respectively. The magnitude and phase responses were measured over a frequency range of 11.5 GHz to 15.5 GHz. FIG. 11 shows the recorded magnitude response, with magnitude shown on the Y axis and given in decibels with reference to a milli-Watt (dBm), and frequency shown on the X axis and given in gigahertz (GHz), with the amplitude being expressed as the ratio between the received, or reflected, microwave energy and the transmitted energy, i.e. the output energy÷input energy. The curve representing the 6 mmol/L glucose concentration is shown using a solid line and the curve representing the 14 mmol/L concentration is shown using a dotted line. It can be seen that a minimum occurs for each concentration and that there is a marked difference in frequency between the positions of said minimums. For the 6 mmol/L glucose concentration the minimum occurs at 13.130 GHz and for the 14 mmol/L glucose concentration the minimum occurs at 13.452 GHz, thus a frequency shift of 322 MHz has been observed here.

Multiple reflections of the microwave field will take place between the faces of the two antennas such that both the net transmitted power and the net reflected power are a result of the phase lag that exists between each reflected wave. This phase lag is a function of both the distance between the antennas, equal to the thickness of the tissue structure, and the real part of the dielectric constant of the tissue structure & biological solution therein (typically blood).

The path difference d, between successive waves is given by:

$$d = 2 \cdot \sqrt{\in_r} \cdot t$$

where $\in$ is the dielectric constant of the material of interest, and t is the physical length of the path in the material. Each reflected wave will lag in phase by an amount given by:

$$\delta = 2\pi 2 \cdot \sqrt{\in_r} \cdot t / \lambda$$

where $\lambda$ is the free space wavelength of the microwave radiation. Both the transmitted power and the reflected power are a result of the superposition of the multiple reflections. The reflected intensity can be represented by Airy's formula and is given by:

$$Ir = \{4 \cdot R \cdot \sin^2(\delta/2)\} / \{(1-R)^2 + 4 \cdot R \cdot \sin^2(\delta/2)\}$$

Where R is the fraction of the intensity reflected on a single reflection. For a lossless medium the transmitted intensity, It, must be given by:

$$Ir = 1 - It$$

And so Airy's formula for the transmitted intensity would be:

$$It=(1-R)^2/\{(1-R)^2+4\cdot R\cdot \sin^2(\delta/2)\}$$

However, the tissue structure is not lossless and the material sample will have a fractional intensity absorption coefficient A. Hence in the formula above (1−R) should be replaced by (1−R−A).

When $\sin^2(\delta/2)=0$, this is a maximum and occurs when:

$$2\cdot\sqrt{\in_r}\cdot t=n\cdot\lambda \text{ } n \text{ being an integer.}$$

However, minima occur at:

$$2\cdot\sqrt{\in_r}\cdot t=(n+1/2)\cdot\lambda$$

FIG. 11 shows the case where a minimum has occurred in the transmitted power and hence the situation represented by this last equation had been set up. The two measured frequencies for the different blood samples can be converted to free space wavelength (λ). Knowing the physical path length of the sample $\in_r$ can be calculated.

A further property of the biological tissue structures that can be utilised in embodiments of the present invention is that the quality factor Q of the tissue varies with the concentration of the constituent to be measured. The quality factor, or Q factor, is a measure of the rate at which a vibrating system dissipates its energy, or alternatively expressed as the ratio of the energy stored in the vibrating system to the energy dissipated. A higher Q factor indicates a lower rate of dissipation. When the system is driven, its resonant behavior depends strongly on Q. Resonant systems respond to frequencies close to their natural frequency much more strongly than they respond to other frequencies. A system with a high Q resonates with a greater amplitude (at the resonant frequency) than one with a low Q factor, and its response falls off more rapidly as the frequency moves away from resonance. This can be seen with reference to FIG. 11, where the amplitude response for the 6 mmol/L solution decays more rapidly away from the minimum than for the 14 mmol/L solution, indicating that the Q factor for the 6 mmol/L solution is higher than that of the 14 mmol/L solution. The Q factor of a system can also be determined from the ratio of the resonant frequency to the −3 dB bandwidth (the frequency bandwidth between the frequencies on either side of the resonant frequency at which the amplitude has decayed by 3 dB [half the peak power] from the resonant peak amplitude). Consequently, in embodiments of the present invention the Q factor for a tissue structure under investigation can be directly derived from the amplitude response and the Q factor correlated to the concentration of the constituent in the tissue structure.

Figure 12:
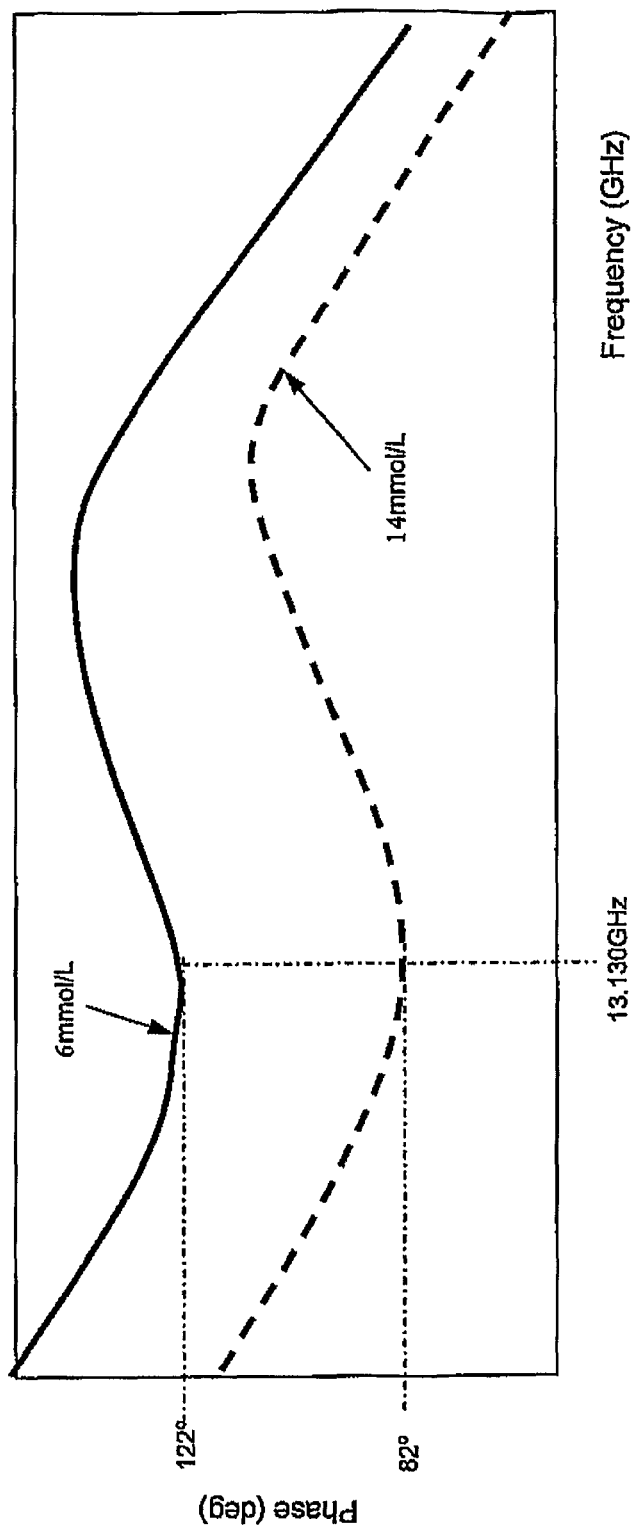
FIG. 12 is a second graph showing phase change results obtained from apparatus according to embodiments of the present invention.

FIG. 12 shows the phase response of the ratio of the received, or reflected, energy to the transmitted energy, where phase is shown on the Y axis and is given in degrees and frequency is shown on the X axis and is given in GHz. The curve representing the 6 mmol/L glucose concentration is shown using a solid line and the curve representing the 14 mmol/L concentration is shown using a dotted line. It can be seen that there is a phase change between the 6 mmol/L glucose concentration and the 14 mmol/L glucose concentration and that the maximum change occurs at a frequency of approximately 13.130 GHz. At this frequency the phase for the 6 mmol/L glucose concentration is 122° and the phase for the 14 mmol/L concentration is 82°, giving a phase difference of 40°. It can be concluded from these result that there is a marked change in the frequency at which a minimum occurs in the magnitude response for two representative blood-glucose concentrations and there is also a marked change in the phase when two blood-glucose solutions of the same volume were measured.

Since there will be a variation in the thickness of the biological tissue structure between individuals, the resonant frequency, and possibly the Q or shape of the transmission curve, of the tissue structure for any given constituent concentration will vary from individual to individual. Therefore, before a valid measurement for an individual can be made it is necessary to know the thickness of the tissue structure. Once the thickness is known, calibration curves can be used to establish the resonant frequency for the structure for various constituent concentrations. A number of methods can be used to automatically measure the thickness:

a) A digital micrometer method;
    b) A measure of change in resistance using a contact to a resistive material;
    c) A low frequency capacitance measurement;
    d) Optical displacement sensor.

In embodiments of the present invention it is convenient to take a low frequency capacitance measurement. To do this it is necessary to assume that the bulk change in relative permittivity of the tissue structure between individuals is negligible at the frequency of interest (for example, 1 KHz or 10 KHz), and that the capacitance is thus directly proportional to the frequency. Consequently, the micro-strip antenna structures of embodiments of the present invention can be used to form the plates of the parallel plate capacitor and a fixed value stable inductor is additionally used to form the low frequency resonant circuit. The capacitor formed by the antenna plates and the biological structure are resonated with the fixed inductor to produce a resonant frequency from which the thickness could be calculated.

The invention claimed is:

1. An apparatus for minimally invasively measuring concentrations of constituents contained within a biological tissue structure, the apparatus comprising:
    a microwave energy source arranged to generate a range of microwave frequencies;
    a first antenna coupled to the microwave energy source and arranged to transmit at least a portion of the microwave energy into the tissue structure;
    a second antenna arranged to receive at least a portion of the microwave energy transmitted through the tissue structure;
    a signal processor arranged to determine the resonant frequency of the received microwave energy; and
    a data processor arranged to provide an output of the concentration of constituents within the biological tissue structure according to the determined resonant frequency.

2. The apparatus according to claim 1, wherein the signal processor is arranged to measure the magnitude response of the ratio of the received microwave energy to the transmitted microwave energy and determine the frequency at which a minima or maxima in the magnitude response occurs, said frequency being the resonant frequency.

3. The apparatus according to claim 2, wherein the signal processor is arranged to determine the 3 dB bandwidth of the magnitude response for the frequency of the minima or maxima and thereby derive the Q factor of the biological tissue structure.

4. The apparatus according to claim 3, wherein the data processor is arranged to correlate the derived value of Q factor to a constituent concentration value.

5. The apparatus according to claim 1, wherein the signal processor is arranged to measure the phase response of the ratio of the received microwave energy to the transmitted microwave energy and determine the frequency at which a minima or maxima in the phase response occurs, said frequency being the resonant frequency.

6. The apparatus according to claim 1, wherein the first and second antennas comprise a single transceiver wherein the received microwave energy comprises reflected microwave energy.

7. The apparatus according to claim 6, wherein the apparatus further comprises a reflector plate arranged to reflect microwave energy transmitted from the single antenna back to said antenna.

8. The apparatus according to claim 1, wherein the microwave energy source is arranged to generate microwave energy over a range of frequencies such that at the resonant frequency the biological tissue structure forms a single wave resonance cavity.

9. The apparatus according to claim 1, wherein the microwave energy source is arranged to generate microwave energy over a range of frequencies such that at the resonant frequency the biological tissue structure forms a half wave resonance cavity.

10. The apparatus according to claim 1, wherein the microwave energy source is arranged to generate microwave energy within the frequency range of 8 GHz to 18 GHz.

11. The apparatus according to claim 10, wherein the microwave source is arranged to generate microwave energy within a number of frequency bandwidths within said frequency range.

12. The apparatus according to claim 1, wherein the first and second antennas comprise patch antennas, each antenna having a radiating patch and a microwave feed line.

13. The apparatus according to claim 12, wherein the microwave feed line comprises a micro-strip connected to the radiating patch.

14. The apparatus according to claim 12, wherein the microwave feed line comprises a coaxial feed.

15. The apparatus according to claim 12, wherein the microwave feed line is electromagnetically coupled to the radiating patch.

16. The apparatus according to claim 12, wherein the radiating patch includes an annular slot formed therein.

17. The apparatus according to claim 1, wherein the first and second antennas comprise spiral antennas.

18. The apparatus according to claim 1 wherein the first and second antennas comprise waveguide antennas.

19. The apparatus according to claim 1, wherein the first and second antennas are arranged to be non-invasively attached to the biological tissue structure.

20. The apparatus according to claim 1, wherein the first and second antennas comprise one of waveguide antennas or coaxial monopole antennas, each antenna having an inner and an outer conductor.

21. The apparatus according to claim 20, wherein the inner antenna comprises a needle like structure arranged to pierce the surface layer of the biological tissue.

22. The apparatus according to claim 21, wherein the inner antenna is hollow and is arranged to be in fluid communication with a fluid source.

23. The apparatus according to claim 21, wherein the outer antenna is arranged to pierce the surface layer of the biological tissue.

24. The apparatus according to claim 1, wherein the data processor is arranged to correlate the determined resonant frequency to the thickness of the biological tissue structure to provide the constituent concentration information.

25. The apparatus according to claim 24, wherein a value for the biological tissue structure thickness is provided as a predetermined input parameter.

26. The apparatus according to claim 24, wherein the signal processor is arranged to measure the capacitance of the biological tissue structure between the first and second antennas, from which the thickness value is derived.

27. The apparatus according to claim 1, wherein said first and second antennas are arranged to be attached to either side of at least one of an earlobe or the skin interconnecting a thumb and forefinger.

28. The apparatus according to claim 1, wherein at least the microwave source, and first and second antennas are arranged as a portable assembly for wearing by an individual.

29. The apparatus according to claim 1, wherein at least one of the signal processor and data processor comprise one from the list of a personal computer, a laptop computer, a mobile computer and a mobile telephone.

30. The apparatus according to claim 1, wherein the constituent concentration comprises at least blood-glucose, blood-alcohol or cholesterol.

31. A method of minimally invasively measuring concentrations of constituents contained within a biological tissue structure, the method comprising:
generating a range of microwave frequencies;
transmitting at least a portion of the generated microwave energy into the tissue structure;
receiving at least a portion of the microwave energy transmitted through the tissue structure;
determining the resonant frequency of the received microwave energy; and
providing an output of the concentration of constituents within the biological tissue structure according to the determined resonant frequency.

32. The method of claim 31, wherein the magnitude response of the ratio of the received microwave energy to the transmitted microwave energy is measured and the frequency at which a minima or maxima in the magnitude response occurs determined, said frequency being the resonant frequency.

33. The method of claim 32, wherein the 3 dB bandwidth of the magnitude response for the frequency of the minima or maxima is determined and therefore the Q factor of the biological tissue structure is derived.

34. The method of claim 33, wherein the derived value of Q factor is correlated to a constituent concentration value.

35. The method of claim 31, wherein the phase response of the ratio of the received microwave energy to the transmitted microwave energy is measured and the frequency at which a minima or maxima in the phase response occurs is determined, said frequency being the resonant frequency.

36. The method of claim 31, wherein the microwave energy generated over a range of frequencies such that at the resonant frequency the biological tissue structure forms a single wave resonance cavity.

37. The method of claim 31, wherein the microwave energy generated over a range of frequencies such that at the resonant frequency the biological tissue structure forms a half wave resonance cavity.

38. The method of claim 31, wherein the microwave energy is generated within the frequency range of 8 GHz to 18 GHz.

39. The method of claim 31, wherein the microwave energy is generated within a number of frequency bandwidths within said frequency range.

40. The method of claim 31, wherein the determined resonant frequency is correlated to the thickness of the biological tissue structure to provide the constituent concentration information.

41. The method of claim 40, wherein a value for the biological tissue structure thickness is provided as a predetermined input parameter.

42. The method of claim 40, wherein the capacitance of the biological tissue structure is measured, from which the thickness value is derived.

43. The method of claim 31, the biological tissue structure comprises one of an earlobe or the skin interconnecting a thumb and forefinger.

44. The method of claim 31, wherein the constituent concentration comprises at least blood-glucose, blood-alcohol or cholesterol.

45. Apparatus for minimally invasively measuring concentrations of constituents contained within a biological tissue structure, the apparatus comprising:
- a microwave energy source arranged to generate a range of microwave frequencies;
- an antenna coupled to the microwave energy source and arranged to transmit at least a portion of the microwave energy into the tissue structure and to receive at least a portion of the microwave energy reflected back;
- a signal processor arranged to measure the magnitude or phase response of the ratio of the received microwave energy to the transmitted microwave energy and determine a frequency at which a minima or maxima in the response occurs, the frequency being a resonant frequency; and
- a data processor arranged to provide an output of the concentration of constituents within the biological tissue structure according to the resonant frequency.

* * * * *